US007397697B2

(12) United States Patent
So et al.

(10) Patent No.: US 7,397,697 B2
(45) Date of Patent: *Jul. 8, 2008

(54) MULTI-BIT-PER-CELL FLASH EEPROM MEMORY WITH REFRESH

(75) Inventors: Hock C. So, Redwood City, CA (US); Sau C. Wong, Hillsborough, CA (US)

(73) Assignee: SanDisk Corporation, Milpitas, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/620,127

(22) Filed: Jan. 5, 2007

(65) Prior Publication Data

US 2007/0104004 A1  May 10, 2007

Related U.S. Application Data

(63) Continuation of application No. 11/101,938, filed on Apr. 7, 2005, now Pat. No. 7,170,781, which is a continuation of application No. 10/045,505, filed on Oct. 18, 2001, now Pat. No. 6,898,117, which is a continuation of application No. 09/680,797, filed on Oct. 6, 2000, now Pat. No. 6,307,776, which is a continuation of application No. 09/200,220, filed on Nov. 25, 1998, now Pat. No. 6,151,246, which is a continuation-in-part of application No. 08/924,909, filed on Sep. 8, 1997, now Pat. No. 5,909,449.

(51) Int. Cl.
*G11C 16/06* (2006.01)

(52) U.S. Cl. ............................ 365/185.09; 365/185.24; 365/222; 365/189.09

(58) Field of Classification Search ............ 365/185.09, 365/185.24, 222, 230.06, 189.09
See application file for complete search history.

(56) References Cited

U.S. PATENT DOCUMENTS 4,139,911 A    2/1979  Sciulli et al.

(Continued)

FOREIGN PATENT DOCUMENTS

| EP | 97460009.0 | 2/1997 |
|---|---|---|
| EP | 0791933 | 8/1997 |
| WO | WO 9012400 | 10/1999 |

OTHER PUBLICATIONS

Communication Pursuant to Article 96(2) EPC for Application No. 98 307 184.6 for SanDisk Corporation dated Aug. 8, 2005, 5 pages.

(Continued)

*Primary Examiner*—David Lam
(74) *Attorney, Agent, or Firm*—Davis Wright Tremaine LLP (57) ABSTRACT

A multibit-per-cell non-volatile memory divides the suitable threshold voltages of memory cells into ranges corresponding to allowed states for storage of data and ranges corresponding to forbidden zones indicating a data error. A read process checks whether a threshold voltage is in a forbidden zone. Alternately, a refresh process includes reprogramming the threshold voltage into an allowed state. In the case of a flash memory, a refresh reads a sector of the memory and saves corrected data from the sector in a buffer or another sector. The corrected data from the buffer or other sector can be written back in the original sector, or the corrected data can be left in the other sector with addresses of the original sector being mapped to the other sector. Refresh process for the non-volatile memory can be performed in response to detecting a threshold voltage in a forbidden zone or periodically.

12 Claims, 5 Drawing Sheets

U.S. PATENT DOCUMENTS

| | | | |
|---|---|---|---|
| 4,218,764 A | 8/1980 | Furuta et al. | |
| 4,253,059 A | 2/1981 | Bell et al. | |
| 4,460,982 A | 7/1984 | Gee et al. | |
| 4,612,630 A | 9/1986 | Rosier | |
| 4,694,454 A | 9/1987 | Matsuura | |
| 4,703,196 A | 10/1987 | Arakawa | |
| 4,703,453 A | 10/1987 | Shinoda et al. | |
| 4,733,394 A | 3/1988 | Giebel | |
| 4,763,305 A | 8/1988 | Kuo | |
| 4,779,272 A | 10/1988 | Kohda et al. | |
| 4,799,195 A | 1/1989 | Iwahashi et al. | |
| 4,809,231 A | 2/1989 | Shannon et al. | |
| 4,827,450 A | 5/1989 | Kowalski | |
| 4,937,787 A | 6/1990 | Kobatake | |
| 4,962,322 A | 10/1990 | Chapman | |
| 4,964,079 A | 10/1990 | Devin | |
| 4,975,883 A | 12/1990 | Baker et al. | |
| 5,052,002 A | 9/1991 | Tanagawa | |
| 5,065,364 A | 11/1991 | Atwood et al. | |
| 5,070,032 A | 12/1991 | Yuan et al. | |
| 5,119,330 A | 6/1992 | Tanagawa | |
| 5,122,985 A | 6/1992 | Santin | |
| 5,132,928 A | 7/1992 | Hayashikoshi et al. | |
| 5,132,935 A | 7/1992 | Ashmore, Jr. | |
| 5,151,906 A | 9/1992 | Sawada | |
| 5,157,629 A | 10/1992 | Sato et al. | |
| 5,172,338 A | 12/1992 | Mehrotra et al. | |
| 5,172,339 A | 12/1992 | Noguchi et al. | |
| 5,200,922 A | 4/1993 | Rao | |
| 5,200,959 A | 4/1993 | Gross et al. | |
| 5,239,505 A | 8/1993 | Fazio et al. | |
| 5,262,984 A | 11/1993 | Noguchi et al. | |
| 5,263,032 A | 11/1993 | Porter et al. | |
| 5,270,551 A | 12/1993 | Kamimura et al. | |
| 5,270,979 A | 12/1993 | Harari et al. | |
| 5,278,794 A | 1/1994 | Tanaka et al. | |
| 5,313,427 A | 5/1994 | Schreck et al. | |
| 5,321,655 A | 6/1994 | Iwahashi et al. | |
| 5,327,383 A | 7/1994 | Merchant et al. | |
| 5,335,198 A | 8/1994 | Van Buskirk et al. | |
| 5,341,334 A | 8/1994 | Maruyama | |
| 5,347,489 A | 9/1994 | Merchant et al. | |
| 5,365,486 A | 11/1994 | Schreck | |
| 5,377,147 A | 12/1994 | Merchant et al. | |
| 5,394,359 A | 2/1995 | Kowalski | |
| 5,450,363 A | 9/1995 | Christopherson et al. | |
| 5,465,236 A | 11/1995 | Naruke | |
| 5,523,972 A | 6/1996 | Rashid et al. | |
| 5,532,962 A | 7/1996 | Auclair et al. | |
| 5,583,812 A | 12/1996 | Harari | |
| 5,621,682 A * | 4/1997 | Tanzawa et al. | 365/185.09 |
| 5,648,934 A | 7/1997 | O'Toole | |
| 5,652,720 A | 7/1997 | Aulas et al. | |
| 5,657,332 A | 8/1997 | Auclair et al. | |
| 5,675,537 A | 10/1997 | Bill et al. | |
| 5,689,465 A | 11/1997 | Sukegawa et al. | |
| 5,703,506 A | 12/1997 | Shook et al. | |
| 5,712,815 A | 1/1998 | Bill et al. | |
| 5,717,632 A | 2/1998 | Richart et al. | |
| 5,751,639 A | 5/1998 | Ohsawa | |
| 5,761,125 A | 6/1998 | Himeno | |
| 5,835,413 A | 11/1998 | Hurter et al. | |
| 5,889,698 A | 3/1999 | Miwa et al. | |
| 5,905,673 A | 5/1999 | Khan | |
| 5,909,449 A | 6/1999 | So et al. | |
| 6,151,246 A * | 11/2000 | So et al. | 365/185.09 |
| 6,199,139 B1 | 3/2001 | Katayama et al. | |

OTHER PUBLICATIONS

Communication Pursuant to Article 96(2) EPC for Application No. 98 307 184.6 for SanDisk Corporation, Aug. 7, 2006, 3 pages.

Lee et al., "Error Correction Technique for Multivalued MOS Memory," *Electronic Letters*, vol. 27, No. 15, Jul. 18, 1991, pp. 1321-1323.

* cited by examiner

MULTI-BIT-PER-CELL FLASH EEPROM MEMORY WITH REFRESH

CROSS REFERENCE TO RELATED APPLICATIONS

This is a continuation of U.S. patent application Ser. No. 11/101,938, filed Apr. 7, 2005, now U.S. Pat. No. 7,170,781, which is a continuation of U.S. patent application Ser. No. 10/045,505, filed Oct. 18, 2001, now U.S. Pat. No. 6,898,117, which is a continuation of U.S. patent application Ser. No. 09/680,797, filed Oct. 6, 2000, now U.S. Pat. No. 6,307,776, which is a continuation of U.S. patent application Ser. No. 09/200,220, filed Nov. 25, 1998, now U.S. Pat. No. 6,151,246, which is a continuation-in-part of U.S. patent application Ser. No. 08/924,909, filed Sep. 8, 1997, now U.S. Pat. No. 5,909,449.

BACKGROUND

1. Field of the Invention

This invention relates to non-volatile semiconductor memory and more specifically to circuits and methods for detecting and correcting data errors in a memory storing multiple bits per memory cell.

2. Description of Related Art

Conventional electrically erasable non-volatile semiconductor memories such as $E^2$PROMs and flash memories have memory cells that include transistors with programmable threshold voltages. For example, a floating gate transistor or a split gate transistor has a threshold voltage that is programmed or erased by charging or discharging a floating gate located between a control gate and a channel in the transistor. The amount of charge on the floating gate of the transistor determines the voltage that must be applied to the control gate to cause charge carrier inversion in the underlying channel and therefore determines the threshold voltage of the transistor. Data is written in such memory cells by charging or discharging the floating gates of the memory cells to achieve threshold voltages corresponding to the data.

A binary memory stores one bit of data per memory cell. Accordingly, floating gate transistors in binary memory cells have two distinguishable states, a high threshold voltage state and a low threshold voltage state. Any memory cell having a threshold voltage above a cut-off threshold voltage value is in the high threshold voltage state and stores a bit value, 1 or 0, that corresponds to the high threshold state. Memory cells having threshold voltages below the cut-off are in the low threshold voltage state and store the bit value, 0 or 1, corresponding to the low threshold voltage state.

A multibit-per-cell memory stores multiple bits per memory cell. Accordingly, a range of threshold voltages for a memory cell is divided into a number of states corresponding to the possible multibit data values stored in the memory cell. For example, a memory that stores two bits of data per memory cell has a range of suitable threshold voltages for memory cells that is divided into four states. A first state includes threshold voltages below a first cut-off. A second state includes threshold voltages between the first cut-off and a second cut-off. A third state includes threshold voltages between the second cut-off and a third cut-off, and a fourth state includes threshold voltages above the third cut-off.

A concern in non-volatile semiconductor memory is drift or unintended changes in the threshold voltages of memory cells. For example, over time, charge tends to leak from the floating gates of memory cells and change the threshold voltages of the cells. Charge leakage decreases the threshold voltage of an N-channel memory cell. Alternatively, a floating gate or an insulator surrounding the floating gate can collect or trap charge and increase the threshold voltage of a cell. Further, operation of the memory, for example, programming or reading stresses memory cells not being accessed and can change threshold voltages. Changes in the threshold voltage are a problem because the state of the memory cell and the data value stored in the memory cell can change and create a data error. Such data errors are intolerable in many memory applications. The problem is worse for multibit-per-cell memories than for binary memories because the range of threshold voltages corresponding to a particular state is typically smaller in a multibit-per-cell memory which makes changes in the state of the memory cell more likely.

Multibit-per-cell memories that are resistant to data errors are sought.

SUMMARY

In accordance with the invention, a range of possible threshold voltages for a memory cell in a multibit-per-cell memory is divided into allowed states associated with data values and forbidden zones between the allowed states. A memory cell being written is programmed into an allowed state. Subsequent reading of the memory cell indicating that the threshold voltage of the memory cell is in a forbidden zone indicates that the threshold voltage of the memory cell has changed and is in error. A memory cell with a threshold voltage in a forbidden zone can be flagged as a data error or corrected by increasing or decreasing the threshold voltage to an adjacent allowed state. One specific embodiment of the invention is a flash memory that presumes charge loss in the memory cells and programs the threshold voltage of a memory cell up to the next allowed state when the memory detects that the threshold voltage of the memory cell is in a forbidden zone. Alternatively, data errors can be corrected by reading the data values from a sector of memory cells including one or more memory cells containing one or more errors, erasing the sector, and then programming the sector with corrected data values.

In accordance with another aspect of the invention, a non-volatile memory performs a refresh cycle in which memory cells are read and threshold voltages of the memory cells are reprogrammed to an allowed state. In a flash EPROM, the refresh cycle can refresh data in a single sector or an entire memory array. In alternative embodiments, the refresh cycle is triggered by external circuit attached to a monolithic integrated circuit memory or is self-triggered in the memory. Refreshes may be performed at periodic intervals of operation, as part of a power-up procedure for the memory, or transparently during each read operation performed by the memory.

According to a further aspect of the invention, adjacent states (i.e., ranges of threshold voltages) for a multibit-per-cell memory cell are mapped to data values using gray coding or another coding system instead of a direct monotonic mapping from threshold voltages to data values. With such coding, a drift from one threshold voltage state to an adjacent threshold voltage state causes only a single bit error. Such single bit errors can be detected and corrected using error correction codes. The gray coding of allowed states can be used with or without forbidden zones between the coded states and/or refresh cycles to correct stored data.

One specific embodiment of the invention is a non-volatile semiconductor memory that includes: an array of memory cells where each memory cell that stores data has a threshold voltage that identifies a multibit data value; an error detection circuit; and a control circuit that controls refresh operations. The error detection circuit detects errors in threshold voltages of memory cells storing data and in response to detecting an error, signals that a memory cell or a memory sector requires a refresh operation. The refresh operation can occur immediately, periodically, during the next start up of the memory, or when the memory becomes inactive for a period of time. During the refresh operation, the control circuit writes a corrected threshold voltage that corrects the error that the error detection circuit detected. The corrected threshold voltage can be written to the original memory cell containing the error or another memory cell that replaces the original memory cell after the refresh operation. The control circuit can read refresh information or an erase count for a sector containing the memory cell having the error and based on the information read select where to write the corrected threshold voltage.

The error detection circuit can detect the error by finding a threshold voltage in a zone forbidden to threshold voltages corresponding to data or from an error detection code stored when the threshold voltage was written. Gray coded allowed threshold voltage states are preferred so that a shift in threshold voltage from one allowed state to a neighboring allowed state causes only a single bit error in the data stored in the memory cell. The memory can further include a data correction circuit that processes an error correction code to identify the corrected threshold voltage to correct the detected error.

Another specific embodiment of the invention is a nonvolatile semiconductor memory including an array of memory cells and a reference voltage generator. In the array, each memory cell that stores data has a threshold voltage that identifies a multibit data value written in the memory cell. The reference generator generates signals indicating bounds of a plurality of ranges of threshold voltages allowed for the memory cells that store data, wherein each range corresponds to a multibit value that differs in only a single bit from a multibit value corresponding to a range that is adjacent in threshold voltage. The reference generator may further generate reference signals indicating bounds of one or more ranges of threshold voltages forbidden for the memory cells storing data. The circuit can also include a control circuit that detects whether the threshold voltage of a memory cell falls in a forbidden range. If a threshold voltage is in a forbidden range, the control circuit corrects a data error by setting the threshold voltage of the original memory cell or a replacement memory cell in an allowed range associated with the value originally written in the original cell.

BRIEF DESCRIPTION OF THE DRAWINGS

Use of the same reference symbols in different figures indicates similar or identical items.

DETAILED DESCRIPTION OF THE PREFERRED EMBODIMENTS

A multibit-per-cell memory in accordance with an embodiment of the invention partitions a range of threshold voltages of a memory cell into a set of allowed states that correspond to data values that can be stored in the memory cell and a set of forbidden zones. The allowed states are separated from each other by forbidden zones so that if the threshold voltage of a memory cell drifts it must cross through a forbidden zone before reaching another allowed state. A memory cell detected as having a threshold voltage in one of the forbidden zones indicates a data error that can be automatically corrected during a read or reported as an error for subsequent correction and refresh procedure.

Figure 1:
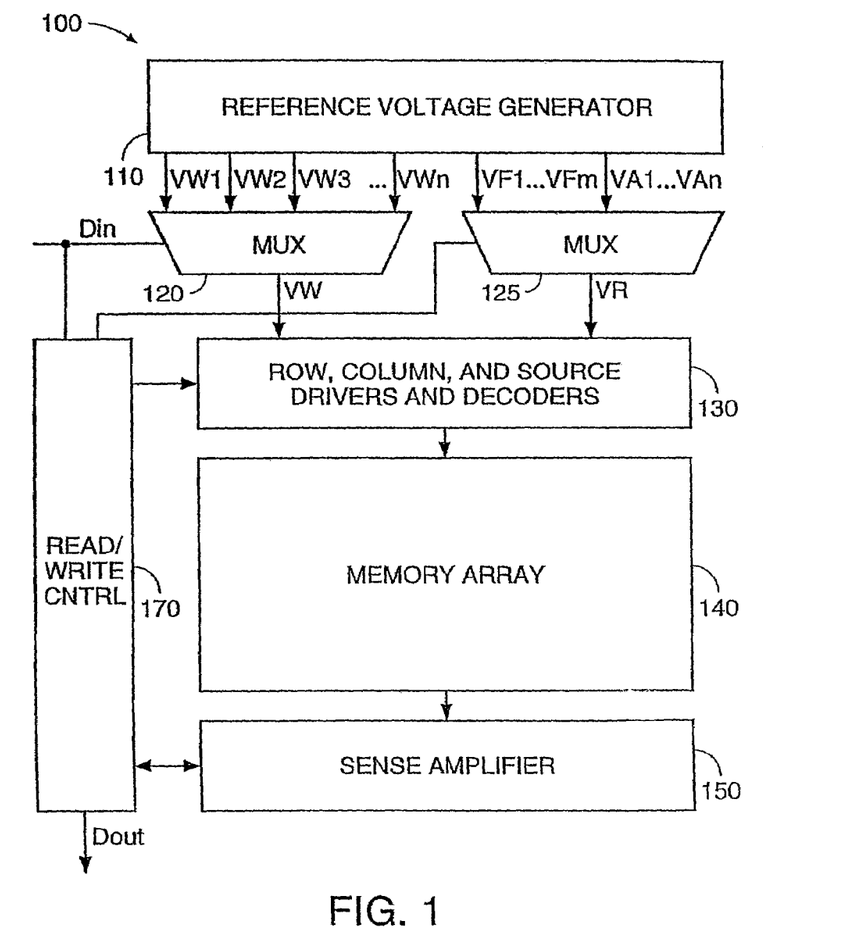
FIG. 1 shows a block diagram of a multibit-per-cell memory in accordance with an embodiment of the invention.

FIG. 1 illustrates a multibit-per-cell memory 100 in accordance with an embodiment of the invention. Memory 100 includes a memory array 140. In an exemplary embodiment of the invention, memory 100 is a flash EPROM, and array 140 includes hundreds or thousands of rows or columns of N-channel floating gate transistors (memory cells) organized into independently erasable sectors. Each row of memory cells has control gates coupled to a row line for the row, and each column of memory cells has drains coupled to a column line for the column. Each erasable sector has a source line coupled to the sources of memory cells in the sector. Row, column, and source drivers and decoders 130 are coupled to memory array 140 and generate voltages that are applied to selected row, column, and source lines in memory array 140 for erase, write, and read operations. For an erase, drivers and decoders 130 apply appropriate voltages to the memory cells in a sector to cause Fowler-Nordheim tunneling that removes electrons from the floating gates and reduces the threshold voltage of the memory cells in the sector. For a write operation, drivers and decoders 130 apply programming voltages to the row, column, and source lines coupled to a target memory cell to cause channel hot electron injection that increases the threshold voltage of the target memory cell to a level indicating a data value being written. As will be understood, applications of the invention. are not limited to flash EPROM of the exemplary embodiment but can be employed in a variety of memory architectures including but not limited to EPROM, $E^2$PROM, and flash $E^2$PROM.

A read/write control circuit 170 controls writing to a target memory cell in memory array 140. For a write, an input digital data signal Din representing a multibit value to be written to the target memory cell is a select signal for a multiplexer 120. Signal Din is restricted to the number of bits that can be written to a single memory cell Data values containing more bits than can be stored in a single memory cell may be split into parts containing the number of bits, e.g., 2, 3, 4 . . . bits, that can be stored in a single memory cell so that the parts can be written sequentially to memory cells using the circuitry shown in FIG. 1 or in parallel using parallel circuits (not shown.) Multiplexer 120, which is coupled to a reference voltage generator 110, selects one of input reference signals VW1 to VWn, where n is the number of possible data values that can be stored in a memory cell. (For example, n is sixteen ($2^x$) for memory storing four bits (x bits) per memory cell.) Multiplexer 120 generates an analog signal VW to drivers and decoders 130 to indicate the value being written.

Figure 2A:
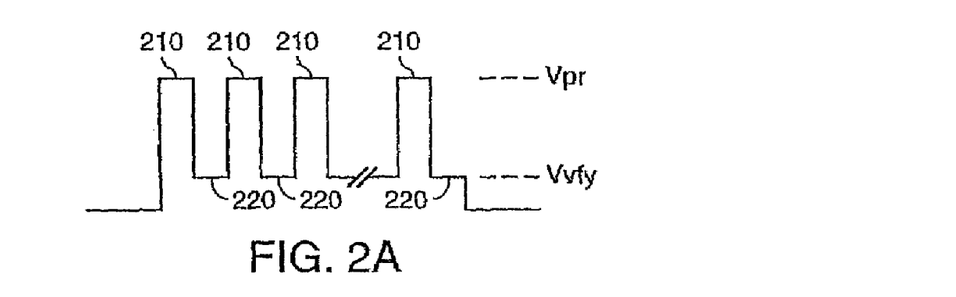
FIGS. 2A and 2B respectively show a row line voltage and a column line voltage during a write operation in the memory of FIG. 1.
Figure 2B:
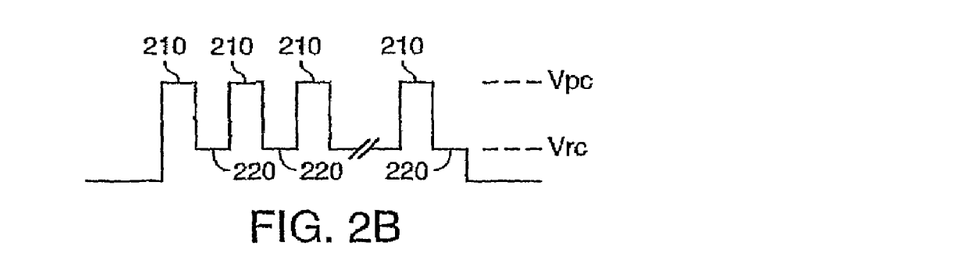

The write process proceeds as illustrated in FIGS. 2A and 2B. In particular, during a series of programming cycles 210, drivers and decoders 130 generate and apply programming voltages Vpr and Vpc to the row and column lines of a target memory cell while. grounding the source line of the sector containing the target cell. In the exemplary embodiment, programming voltage Vpr is between 7 and 11 volts and depends on signal VW. Drivers and decoders 130 may include, for example, a row line driver containing voltage shifter or amplifier having signal VW as an input signal and voltage Vpr as an output signal. Alternatively, voltage Vpr may be a fixed voltage, independent of signal VW. A conventional row decoder applies voltage Vpr to the row line coupled to the target memory cell. A conventional column decoder applies voltage Vpc to the drain of the target memory cell during programming cycles 210. Voltage Vpc is typically about 6 volts or whatever voltage is required to increase the threshold voltage of the target memory cell by channel hot electron (CHE) injection of electrons into the floating gate of the target memory cell. Alternative embodiments of the invention using, for example, $E^2PROM$ technology program memory cells by tunneling instead of CHE injection.

Verify cycles 220 between programming cycles 210 determine whether the threshold voltage of the target memory cell has reached the desired level. During each verify cycle, drivers and decoders 130 apply to the control gate of the target memory cell a voltage Vvfy which depends on (or is equal to) voltage VW (i.e., one of reference voltages VW1 to VWn), grounds the source lines, and applies a read voltage Vrc to the column line of the target memory cell. A sense amplifier 150 senses whether the target memory cell conducts. If the target memory cell conducts during a verify cycle 220, the threshold voltage of the memory cell is less than voltage Vvfy, and read/write control 170 starts another programming cycle 210 to further increase the threshold voltage. If the target memory cell does not conduct during a verify cycle 220, the threshold voltage has exceeded (but is about equal to voltage Vvfy), and read write control 170 stops further programming cycles 220.

Figure 3A:
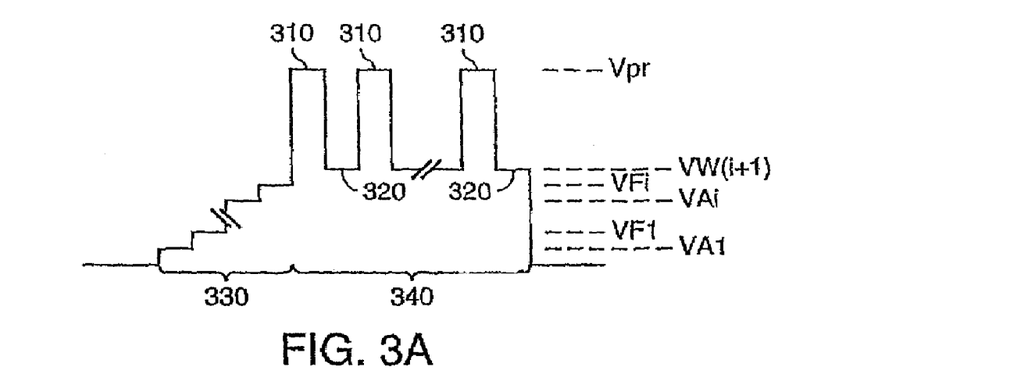
FIGS. 3A and 3B respectively show a row line voltage and a column line voltage during a read/refresh operation in the memory of FIG. 1.
Figure 3B:
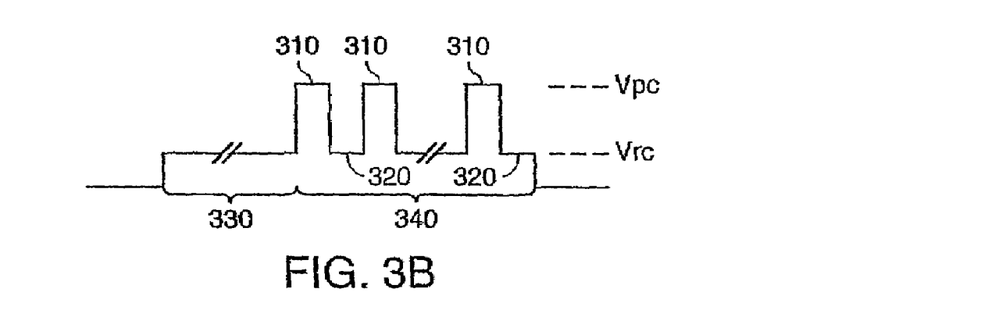
Figure 4A:
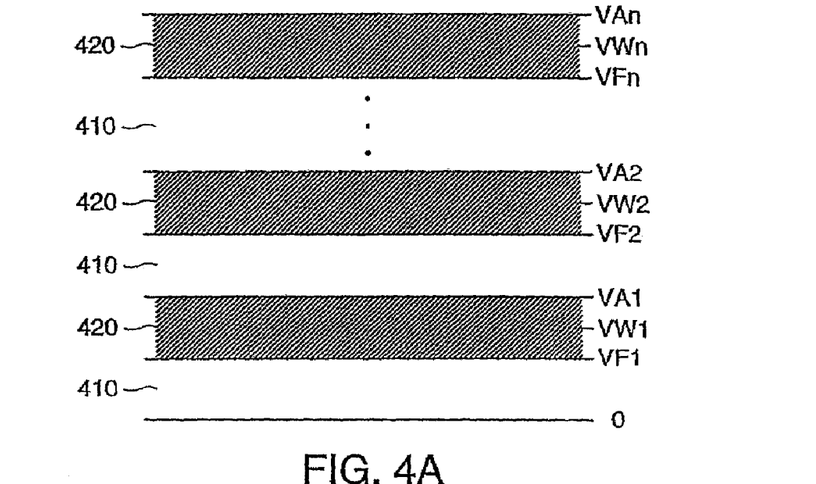
FIGS. 4A and 4B show partitions of threshold voltage ranges into allowed states and forbidden zones in accordance with an embodiment of the invention.

Read/write control 170 also controls read and refresh processes in accordance with an embodiment of the invention. FIGS. 3A and 3B respectively show a row line voltage and a column line voltage during an exemplary combined read/refresh process performed on a target memory cell. During a read stage 330 of the read/refresh process, drivers and decoders 130 ground the source lines, apply a constant read voltage Vrc (typically about 1 to 2 volts) to the column line coupled to the target memory cell, and apply a series of reference voltages from reference voltage generator 110 to the row line (and therefore the control gate) of the target memory cell. For each reference voltage applied to the row line during read stage 330, sense amplifier 150 senses whether the target memory cell conducts. The applied reference voltages during read stage 130 indicate the bounds of allowed threshold voltage states and of forbidden threshold voltage zones such as illustrated in FIG. 4A. In FIG. 4A, reference voltages VF1 to VFm mark the upper bounds of forbidden zones 410 and the lower bounds of allowed threshold voltage states 420. Reference voltages VA1 to VAn mark the upper bounds of allowed threshold states 420 and the lower bounds of forbidden zones 410. Each of the reference voltage levels VW1 to VWn are within an associated one of allowed states 420 so that a write operation ends with a threshold voltage of a target memory cell being in the allowed state 420 associated with the reference voltage VW. Voltage levels VW1 to VWn are not necessarily at the center of an associated allowed state 420. Depending on memory cell characteristics, reference voltage levels VW1 to VWn can be near the top (if charge loss is the dominant effect) or near the bottom (if charge gain is dominant effect) of the associated allowable zones 420. Such an arrangement maximizes the chance that the threshold voltage of a memory cell will remain in an allowed zone 420 and be read correctly. To provide the desired reference voltages as shown in FIG. 4A (or 4B), reference voltage generator 110 may contain a voltage source coupled to series connected resistive elements with taps between the resistive elements for the reference voltages VW1 to VWn, VF1 to VFm, and VA1 and VAn.

During read stage 330, read/write control 170 uses multiplexer 125 to select reference voltages applied to through drivers and decoders 130 to the row line coupled to the target memory cell. Reference voltages starting with lowest reference voltage (voltage VF1 in FIG. 4A) are sequentially applied in order of increasing voltage until sense amplifier 150 senses that applied voltage VR causes the target memory cell to conduct. Thus, at the end of read stage 330, voltage VR is upper bound of the allowed state or forbidden zone containing the threshold voltage of the target memory cell. An alternative read process to that shown in FIGS. 3A and 3B starts at the maximum reference voltage VAn and proceeds in order of decreasing threshold voltage to find a lower bound of the allowed state or forbidden zone containing the threshold voltage of the target memory cell. Yet another read process starts at a reference voltage in the middle of the range of reference voltages and identifies which half (upper or lower) of the range contains the target threshold voltage. (If the memory cell conducts when the middle reference value is applied, the threshold voltage of the target memory cell is in the lower half. Otherwise the threshold voltage of the target memory cell is in the upper half.) Second and if necessary third and subsequent reference voltages applied to the control gate are in the middle of the range previously identified as containing the threshold voltage of the target memory cell. Sensing for these threshold voltages identifies which quarter, eighth, or smaller division of the threshold voltage range contains the threshold voltage of the target cell. When the division identified is a single allowed state or forbidden zone, the reference voltage that is just above the threshold voltage of the target memory cell is identified. An advantage of the last read process is an on-average decrease in the number of reference voltages applied and sensed from $2^{x-1}$ to x where x is the number of bits stored per memory cell. Thus, the last read process provides better average performance for memory storing more than two bits per memory cell.

Voltage VR at the end of read stage 330 indicates the upper bound of either an allowed state or a forbidden zone containing the threshold voltage of the target memory cell. Read/write control 170 generates a multibit digital data signal Dout based on the bound that voltage VR identifies. If voltage VR at the end of read stage 330 is an upper bound of an allowed state, signal Dout indicates the multibit value associated with that state. If voltage VR is an upper bound of a forbidden zone, value Dout indicates the multibit value associated with the allowed state just above the forbidden zone containing the threshold voltage of the memory cell. Thus, this read process assumes that the threshold voltage of the target memory drifted down which is the most common type of change in threshold voltage for N-channel floating gate transistors. If voltage VR is the upper bound of an allowed threshold voltage state at the end of read stage 330, the read/refresh process is complete. No refresh is required. However, if as in FIGS. 3A, voltage VR is the upper bound of a forbidden zone, a refresh stage 340 of the read/refresh process begins.

During refresh stage 340, programming cycles 310 and verify cycles 320 raise the threshold voltage of the target memory cell to the next higher threshold 30 voltage state. In the particular example of FIGS. 3A and 3B, voltage VR is equal to reference voltage VFi at the end of read stage 330, and signal Dout identifies the multibit value corresponding to the next greater allowed level and to reference voltage VW(i+1). Read/write control 170 feeds signal Dout back to multiplexer 120 which sets voltage VW equal to the reference voltage VW(i+1). Thus, during programming cycles 310 and verify cycles 320, programming voltage Vpr and verify voltage Vvfy are appropriate for the value being refreshed. As in the write process described above, programming cycles 310 continue until a verify cycle 320 indicates that the threshold voltage of the target cell has reached the level of reference voltage VW(i+1) after which refresh stage 340 is complete.

Figure 5:
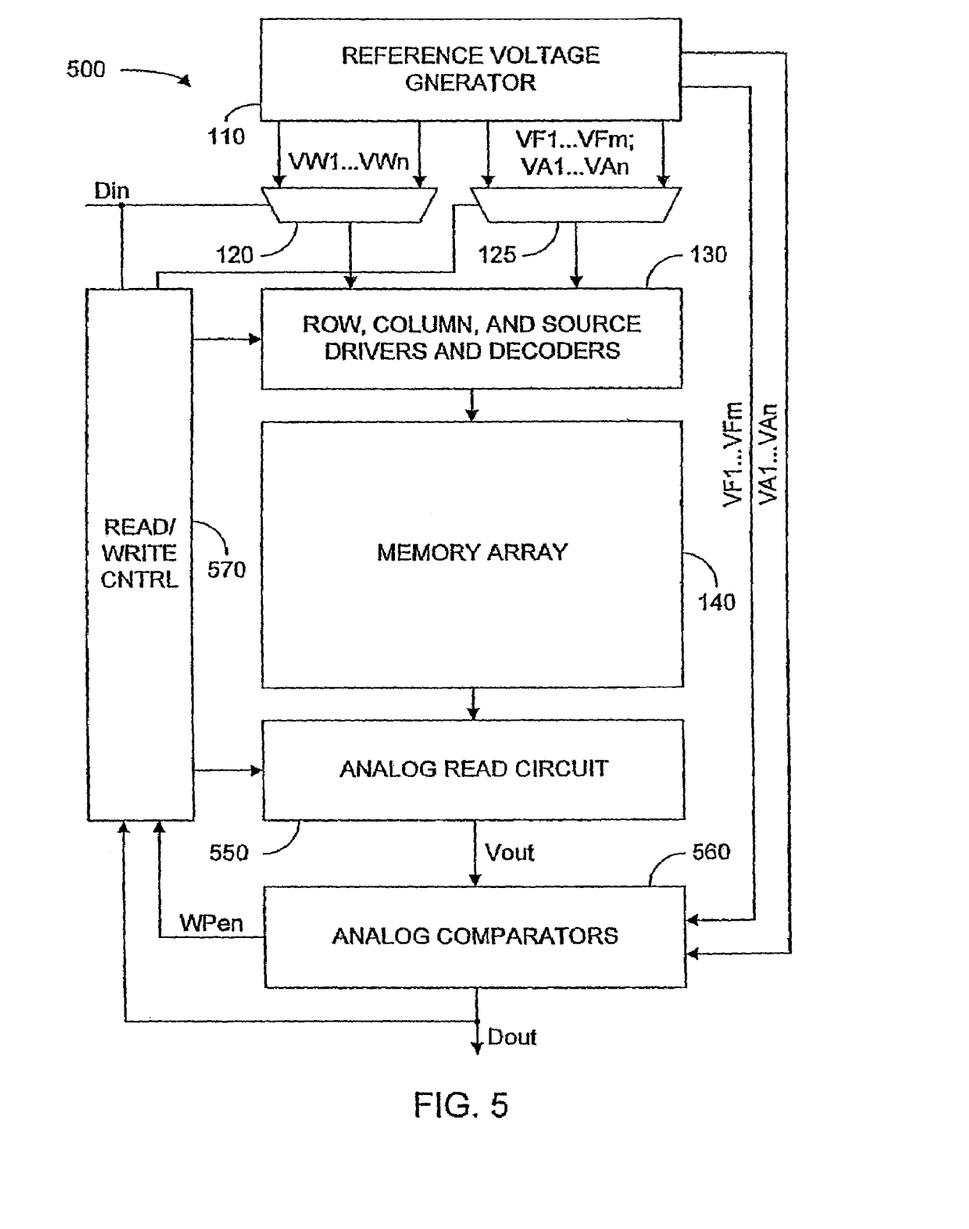
FIG. 5 shows a block diagram of a multibit-per-cell memory in accordance with another embodiment of the invention.

FIG. 5 shows an alternative multibit-per-cell non-volatile memory 500 in accordance with an embodiment of the invention. Memory 500 differs from memory 100 of FIG. 1 primarily in that a read uses an analog read circuit 550 and comparators 560, not sense amplifiers 150. In particular, instead of repeatedly sensing whether the target memory cell conducts when a series of different reference voltages is applied to the control gate of the memory cell, analog read circuit 550 generates an analog voltage Vout that indicates the threshold voltage of the target memory cell. In an alternative embodiment, analog read circuit generates a signal having a current that indicates the threshold voltage of a target memory cell. U.S. Pat. No. 5,751,635, entitled "Read Circuits for Analog Memory Cells"; U.S. Pat. No. 5,748,534, entitled "Feedback Loop for Threshold Voltage Measurement"; and U.S. Pat. No. 5,748,533, entitled "Read Circuit that uses a Coarse-to-Fine Search when Reading the Threshold Voltage of a Memory Cell" describe suitable analog read circuits and are incorporated by reference herein in their entirety. Analog comparators 560 operate in parallel to compare voltage Vout to reference voltages VA1 . . . VAn and VF1 . . . VFN. From the results of the comparisons, logic (not shown) coupled to analog comparators 150 determines which is the smallest reference voltage greater than voltage Vout and generates digital output signal Dout. The architecture of memory 500 typically provides faster reads than memory 100 if generating signal Vout is faster than applying a series of reference voltages.

Alternatively, analog comparators 560 include one comparator or fewer comparators than there are references voltages VA1 . . . VAn and VF1 . . . VFN, and the comparator or comparators sequentially compare voltage Vout to each references voltages VA1 . . . VAn and VF1 . . . VFN. Any sequence of comparisons can be made. For example, comparisons searching for the nearest reference voltage can start from a highest, lowest, or middle reference voltage and proceed until the range containing Vout is found. This embodiment of the invention can decrease circuit size and cost but increases the read time.

Figure 4B:
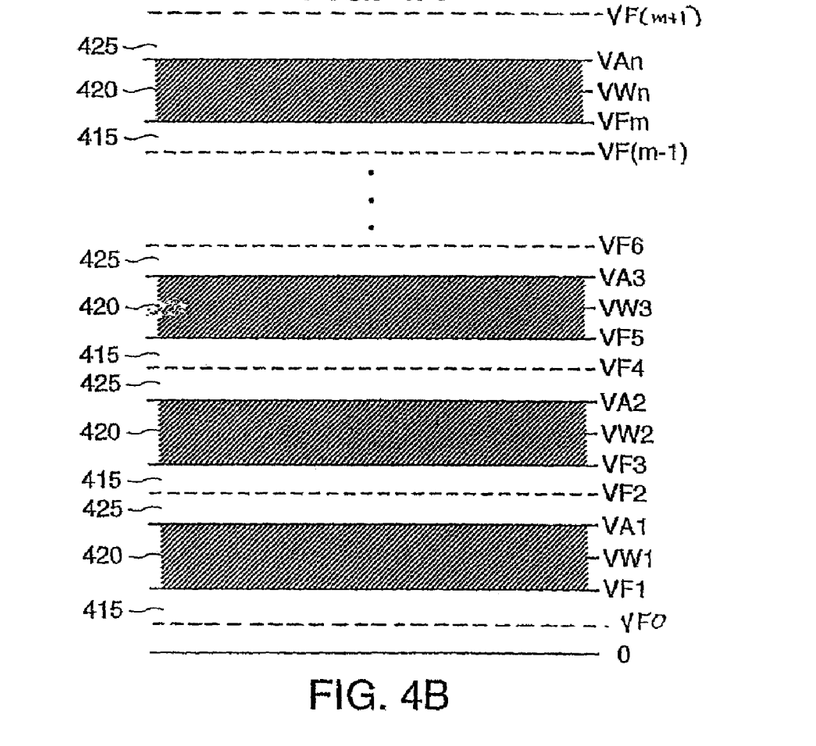

The write/refresh process described above assumes that a threshold voltage in a forbidden zone indicates a memory cell that leaked charge which decreased the threshold voltage of the memory cell. However, threshold voltages can also increase as the result of charge trapping in a floating gate or in the insulator surrounding the floating gate. FIG. 4B illustrates reference voltage levels VF1 to VFm that define two forbidden zones 415 and 425 between each adjacent pair of allowed states 420. Each forbidden zone 415 is just below an adjacent allowed state 420. Each forbidden zone 425 is just above an adjacent allowed state 420. In accordance with this embodiment of the invention, a data error that occurs when a memory cell has a threshold voltage in one of forbidden zones 415 is presumed to result from charge loss from a memory cell originally in the adjacent higher allowed state 420. Thus, read/write control 170 or 570 decodes a threshold voltage in a forbidden zone 415 as data values corresponding to the next higher allowed state 420. A threshold voltage in one of forbidden zones 425 is presumed to result from charge trapping or another mechanism increasing the threshold voltage from the adjacent lower allowed state 420. Additional forbidden zones bounded by voltage levels VF0 and VF(m+1) at the extremes of the normal threshold voltage range are for detecting "hard defects." For example, if the threshold voltage range of memory cells of properly operating memory cells is from 1.0 volt to 5.0 volts, a threshold voltage much less than 1.0 volt or much higher than 5.0 volts indicates that a memory cell may be stuck at a low or high threshold voltage. A spare memory cell or spare sector can replace a stuck memory cell or a sector containing the stuck memory cell.

The sizes of allowed states 420 and forbidden zones 415 and 425 can differ from one state or zone to the next. For example, if charge loss is the dominant factor in change of threshold voltages, the threshold voltage range for the forbidden zone 415 below an allowed state 420 can be larger than the threshold voltage range of the forbidden zone 425 above the allowed state 420. Furthermore, memory cells with higher threshold voltage tend to lose charge faster. Accordingly, the size of allowed states 420 and forbidden zones 415 and 425 can vary with the threshold voltages in the states or zones. Further, reference voltage generator 110 can also adjust the boundaries of zones 415, 420, and 425 dynamically, for example, as a function of temperature, supply voltage, time since the last refresh of the sector, the number of erase/write cycles associated with a sector, or even the threshold voltage read during the last read cycle.

Figure 6:
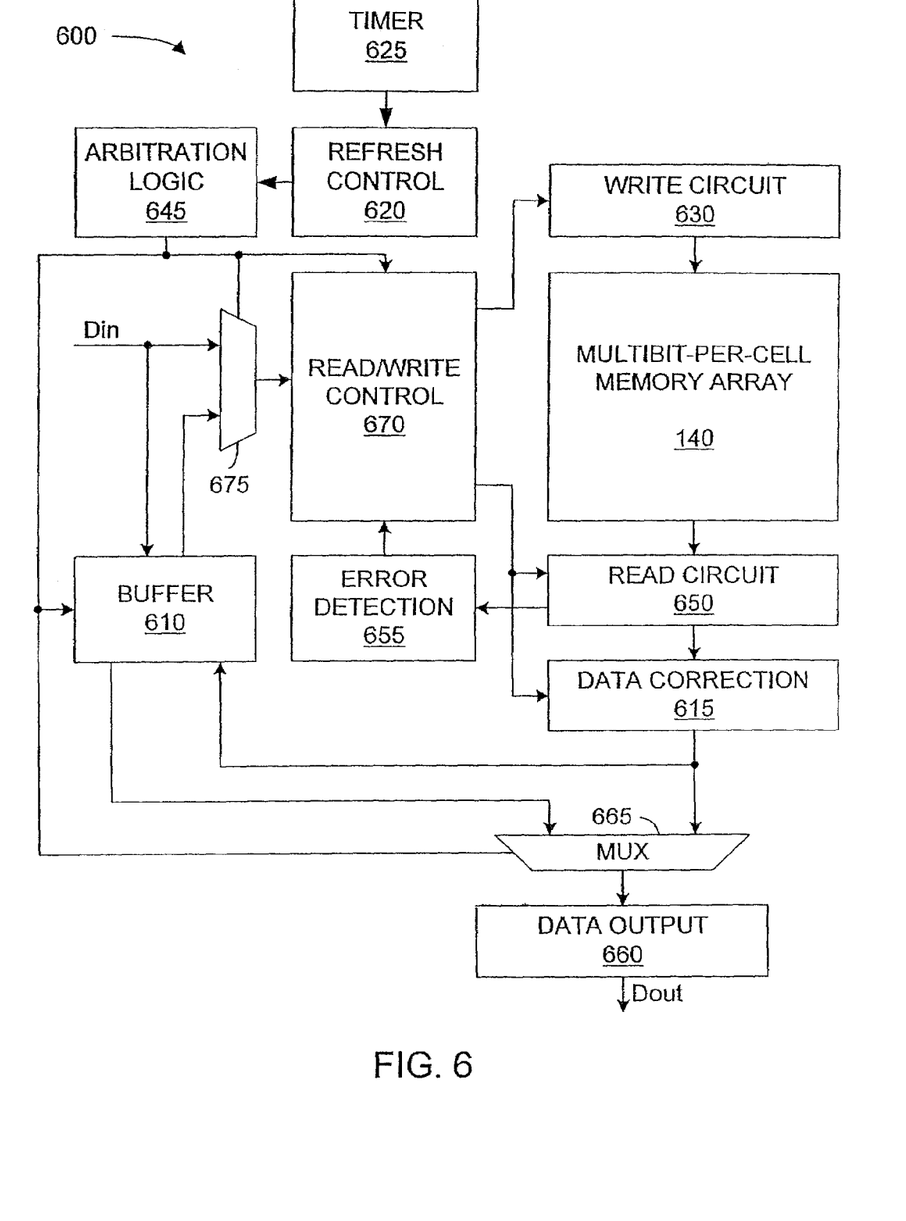
FIG. 6 shows a block diagram of a multibit-per-cell non-volatile memory system with refresh circuits in accordance with an embodiment of the invention.

Read/write control 170 or 570 decodes a threshold voltage in a forbidden zone 425 as data values corresponding to the next lower allowed state 420. Threshold voltages in forbidden zones 415 can be corrected by programming the memory cell up to the next allowed state. Similarly, if a memory architecture provides a method for individual erasing or reducing the threshold voltage of a single memory cell, a threshold voltage in a forbidden zone 425 can be lowered to the next lower allowed state. However, a typical flash memory architecture erases a sector as a unit and does not provide a mechanism for erasing or reducing the threshold voltage of individual memory cells. In such flash architectures, a sector containing a data error can be marked as requiring a refresh. Special memory cells in the array or a separate register can be used to identify the data sectors marked for a refresh. FIG. 6 illustrates a system 600 capable of performing scheduled or delayed refreshes of sectors. In system 600, an error detection circuit 655 detects data errors in data that a read circuit 650 reads from memory array 140. Error detection can occur as described above when a read circuit 650 reads a memory cell having a threshold voltage in a forbidden zone or as described below when a data value read is inconsistent with an error detection and correction code. When an error is detected, error detection circuit 655 marks the sector as requiring a refresh, for example by directing read/write control 670 to write a flag value in overhead memory cells in the sector containing the data error or write a sector number in a register in a refresh control 620. The refresh for a data sector marked as containing a data error need not be immediate. Instead refresh control 620 can wait for a period of inactivity of memory 600 before initiating a refresh operation on the marked sector. Alternatively, if the flag is stored in non-volatile memory, the refresh operation can occur during a start up procedure in which refresh control 620 checks for sectors requiring a refresh operation.

To perform a refresh operation on an identified sector, refresh controller 620 reads the identified sector and temporarily stores the results in a buffer 610 while the identified data sector is erased. Buffer 610 can be on-chip or off-chip volatile memory such as SRAM or DRAM or non-volatile memory that stores digital or analog data. A digital buffer stores digital values that a data output circuit 660 determines from the threshold voltage of the identified sector. In one embodiment of memory 600, read circuit 650 is an analog read circuit, and data output circuit 660 includes an analog-to-digital converter provides digital results for storage in data buffer 610. Use of an analog buffer can avoid such conversions during a refresh. For example, if buffer 610 contains DRAM cells, charge stored in DRAM capacitors may be proportional to the threshold voltages read from associated multibit-per-cell memory cells, and analog values read from the DRAM cells can indicate the threshold voltage to be programmed. However, analog. DRAM requires additional overhead circuitry. Another alternative is to use a spare memory sector in array 140 for buffer 610 so that the same analog read and write circuits 650 and 630 can read from the selected sector and write to the spare sector. Data from the spare sector can be rewritten to the original sector after the original sector has been erased. Alternatively, data can be left in the spare sector with addresses initially corresponding to the original sector being mapped to the spare sector.

Refresh control 620 controls refresh operations that read the content of a data sector into buffer 610, correct the data, and write data from buffer 610 back to memory array 140. In the case where threshold voltages are recorded in buffer 610, a data correction circuit 615 identifies any threshold voltages that are not in an allowed state 420 and replaces such threshold voltages with the correct one of target levels VW1 to VWn. If error detection and correction codes are used instead of or in addition to forbidden zones, data correction circuit 615 can also use such codes to determine or confirm the correct data value or correct threshold voltage. As shown, correction circuit 615 operates on digital values read from memory array 140, but alternatively data correction can be performed before writing values from buffer 610 to a sector in array 140.

The corrected data can be written back into the original sector or to a different sector. Using a different sector helps to "randomize" the number of write/erase cycles for each sector. Otherwise, "bad" sectors that require frequent refresh operations would be subject to more program and erase cycles than "good" sectors, and the refresh operations could exacerbate endurance problems. To determine when a different sector should store the corrected values after a refresh, overhead memory cells in each sector can hold an erase count indicating the number of write/erase cycles for the sector and/or a refresh time indicating when the sector was last refreshed. Each erase cycle reads the erase count from a sector, erases the sector, and stores an incremented erase count in the overhead memory cells. Each refresh operation updates the refresh time in the sector. A sector can be declared invalid or defective during a refresh operation when the erase count is too high or when the last refresh time indicates a very short interval since the last refresh operation. The erase count is too high, for example, when the erase count exceeds a limit predetermined for the memory or determined relative to the erase counts in other sectors. When the erase count is too high or the last refresh was too recent, a refresh operation uses a spare sector in place of the invalid sector. An alternative implementation uses a new sector for each refresh operation. For both embodiments, an on-chip or off-chip control circuit can keep track of the address mappings when swapping sectors.

During the refresh of a sector, arbitration logic 645 can perform arbitration to avoid accessing of a sector being erased. For example, memory 600 may be flagged as temporarily unavailable. Alternatively, as illustrated in FIG. 6, arbitration logic 645 can reroute data accesses. For a write, arbitration logic 645 temporarily stores input data and possibly an address in buffer 610 and after a refresh operation is complete, controls multiplexer 675 to write the data from buffer 610 to the indicated address. If buffer 610 contains the data corresponding to a read address, arbitration logic 645 controls a multiplexer 675 to route data from buffer 610 to data output circuit 660 during a refresh operation.

System 600 also includes a timer 625 for systematic memory refreshes and delaying flagged refreshes until a convenient time. In alternative embodiments of the invention, timer 250 is on-chip or is an off-chip component. As described above, a refresh operation affects a single memory cell or sector, but an entire memory can be refreshed sector by sector if desired. Such refreshes can keep data accurately stored in non-volatile memory for extended periods of time even if the data is not otherwise read periodically. In one embodiment of the invention, memory refreshes are periodic with a period shorter than the time required for a non-defective memory cell to drift from one allowed state, across a forbidden zone to another allowed state or a forbidden zone corresponding to another allowed state. Such periods are typically on the order of at least weeks or months for current non-volatile memory but more frequent refreshes having a period of on the order of a day or less can be used. Because of the long intervals between refreshes, periodic memory refreshes may be scheduled for times when use of the memory is less likely. Selection of the time for a refresh can be selected according to the time of the day or the day of the week to select a time when memory access is unlikely, for example, midnight on a Sunday. Refresh control 620 can also monitor memory access to select and further delay a refresh until detecting a suitably long period of memory inactivity. The last date and time of a refresh can be stored on-chip and checked periodically when the memory is powered. Additionally or alternatively, refresh control 620 can conduct a full or partial refresh of memory array 140 as part of a power-up procedure for memory 600.

As another aspect of the invention, a mapping between allowed threshold voltage states and digital values maps adjacent threshold voltage levels to multibit values that differs only in a single bit. Accordingly, the threshold voltage of a memory cell drifting from one threshold voltage state to an adjacent state causes a single bit error. In contrast, for conventional data coding, which monotonically maps threshold voltage states with increasing (or decreasing) threshold voltage to sequentially increasing binary values, a memory cell's threshold voltage drifting a single state can cause a multibit error.

Table 1 illustrates two data coding schemes for a multibit-per-cell memory that stores one 4-bit value per memory cell. To store a 4-bit value in a memory cell, sixteen allowed states are allocated in the range of possible (or suitable) threshold voltages for the memory cell. For Table 1, a threshold voltage ranging between 1 and 5 volts is partitioned into sixteen allowed states designated levels 1 to 16.

TABLE 1

16-bit Linear and Gray Coded States

| LEVEL | THRESHOLD VOLTAGE | LINEAR CODING | GRAY CODING |
|---|---|---|---|
| 1 | 1.00-1.24 V | 0000 | 0000 |
| 2 | 1.25-1.49 V | 0001 | 0001 |

TABLE 1-continued 16-bit Linear and Gray Coded States

| LEVEL | THRESHOLD VOLTAGE | LINEAR CODING | GRAY CODING |
|---|---|---|---|
| 3 | 1.50-1.74 V | 0010 | 0011 |
| 4 | 1.75-1.99 V | 0011 | 0010 |
| 5 | 2.00-2.24 V | 0100 | 0110 |
| 6 | 2.25-2.49 V | 0101 | 0111 |
| 7 | 2.50-2.74 V | 0110 | 0101 |
| 8 | 2.75-2.99 V | 0111 | 0100 |
| 9 | 3.00-3.24 V | 1000 | 1100 |
| 10 | 3.25-3.49 V | 1001 | 1101 |
| 11 | 3.50-3.74 V | 1010 | 1111 |
| 12 | 3.75-3.99 V | 1011 | 1110 |
| 13 | 4.00-4.24 V | 1100 | 1010 |
| 14 | 4.25-4.49 V | 1101 | 1011 |
| 15 | 4.50-4.74 V | 1110 | 1001 |
| 16 | 4.75-4.99 V | 1111 | 1000 |

The linear coding according of Table 1 maps threshold voltage levels 1 to 16 in order of increasing threshold voltage to sequentially increasing binary values 0000 to 1111. With linear coding, if the threshold voltage of a memory cell is programmed to threshold voltage level 9 but drifts down to threshold voltage level 8, a 4-bit error occurs. In contrast, for the gray coding of Table 1, a threshold voltage drifting to an adjacent allowed state causes only a single bit error.

To implement the gray coding of Table 1 in memory array 100 of FIG. 1, multiplexer 120 implements the mapping between a 4-bit digital value Din as in column 4 of Table 1 to a voltage VW that is within a voltage range indicated in column 2 of Table 1. Read/write control 170 performs the reverse mapping from VR at the end of the read stage the associate digital value in column 4 of Table 1.

The gray coding process of Table 1 can be varied in a variety of ways. For example, many different mappings that provide a series of values where adjacent values differ by a single bit are possible. Such mappings are not restricted to 4-bit data values but are known for any size of multibit data values. Also, although Table 1 describes allowed states which are separated by 0.01-volt forbidden zones, gray coding of multibit values in a memory cell is applicable to memories where possible threshold voltages for a memory cell do not have forbidden zones between the allowed states.

As a further aspect of the invention, error detection and correction codes can be generated and stored for a section, row, column, or other part of a memory and used to correct data errors. In particular, when a threshold voltage is observed in a forbidden zone (e.g., between 2.99 volts and 3.00 volts), an error correction code generated when data was written can be used to determine the correct allowed threshold voltage state for a memory cell. The gray coding of Table 1 is well suited to use with error correction codes since single bit errors are typically easier to correct with error correction codes than are multiple bit errors. In memory 600 of FIG. 6, error detection circuit 655 use error detection codes to detect errors with or without forbidden zones and when the threshold voltage of a memory cell has crossed through a forbidden zone. Similarly, data correction circuit 615 corrects data or threshold voltages using error correction codes with or without-forbidden zones and when the threshold voltage of a memory cell has crossed through a forbidden zone.

Although the invention has been described with reference to particular embodiments, the description is only an example of the invention's application and should not be taken as a limitation. In particular, even though much of preceding discussion was aimed at non-volatile memory including N-channel floating gate devices, alternative embodiments of this invention include other memory structures. For example, embodiments employing P-channel transistors are possible. In such embodiments, erasing and charge leakage increase the threshold voltage of a memory cell, and programming decreases the threshold voltages. Accordingly, variations in the read and write processes described above are required. Various other adaptations and combinations of features of the embodiments disclosed are within the scope of the invention as defined by the following claims.

We claim:

1. A non-volatile semiconductor memory comprising:
   an array of memory cells;
   drivers and decoders coupled to apply voltages to the array to read any memory cell in the array, wherein each memory cell that stores data has a threshold voltage corresponding to a range of threshold values that identifies a multibit data value written in the memory cell, wherein the ranges of threshold values that identify data values are separated from each other by at least one range of threshold values corresponding to errors in the threshold voltages of memory cells storing data;
   an error detection circuit that detects errors in threshold voltages of memory cells storing data, wherein in response to detecting an error in the threshold voltage of a memory cell, the error detection circuit signals for a refresh operation;
   a control circuit coupled to control the drivers and decoders, wherein during the refresh operation, the control circuit writes a corrected threshold voltage that corrects the error that the error detection circuit detected.

2. The memory of claim 1, wherein the control circuit writes the corrected threshold voltage to the memory cell in which the error detection circuit detected the error.

3. The memory of claim 1, wherein the control circuit writes the corrected threshold voltage to a memory cell other than the memory cell in which the error detection circuit detected the error.

4. The memory of claim 3, further comprising an address mapping circuit that accounts for an address mapping, wherein when the control circuit writes the corrected threshold voltage to the other memory cell, the address mapping circuit changes the address mapping to indicate a new physical location for the corrected threshold voltage.

5. The memory of claim 1, wherein the control circuit reads refresh information for a sector containing the memory cell having the error in the threshold voltage and based on the refresh information selects where to write the corrected threshold voltage.

6. The memory of claim 1, wherein the control circuit reads a count of erase cycles for a sector containing the memory cell having the error in the threshold voltage and based on the count selects where to write the corrected threshold voltage.

7. The non-volatile memory of claim 1, wherein the error detection circuit comprises:
   a reference generator that generates first reference signals and second reference signals, the first reference signals indicating bounds of ranges of threshold voltages allowed for the memory cells storing data, and the second reference signals indicating bounds of one or more forbidden ranges of threshold voltages corresponding to said errors in threshold values of memory cells storing data; and
   a circuit that determines whether a threshold voltage of a memory cell is in one of the ranges allowed or one of the ranges forbidden.

8. The non-volatile memory of claim 1, wherein the error detection circuit processes an error detection code to identify a data error in data read from the array, the data error indicating the threshold voltage error in the memory cell.

9. The non-volatile memory of claim 1, further comprising a data correction circuit that processes an error correction code to identify the corrected threshold voltage.

10. A non-volatile semiconductor memory comprising:

an array of memory cells;

drivers and decoders coupled to apply voltages to the array to read any memory cell in the array, wherein each memory cell that stores data has a threshold voltage that identifies a multibit data value written in the memory cell; and a reference generator that generates signals indicate bounds of a plurality of ranges of threshold voltages allowed for the memory cells that store data, wherein each range in the plurality corresponds to a multibit value that differs in only a single bit from a multibit value corresponding to a range that is adjacent in threshold voltage, and wherein the reference generator further generates reference signals indicating bounds of one or more forbidden ranges of threshold voltages corresponding to data errors, wherein the allowed ranges of threshold voltages are separated from each other by at least one forbidden range.

11. The memory of claim 10, further comprising a control circuit coupled to control the drivers and decoders, wherein during a refresh operation, the control circuit detects whether the threshold voltage of the memory cell is in a range forbidden for memory cells storing data, and sets the threshold voltage of a memory cell in the array into one of the ranges allowed for memory cells storing data.

12. The memory of claim 10, further comprising a control circuit coupled to control the drivers and decoders, wherein during a refresh operation, the control circuit detects whether data stored a memory cell contains a data error, uses a error correction code stored in the memory array to identify a correct data value for the memory cell, and sets the threshold voltage of a memory cell in the array into the range corresponding to the correct data value.

* * * * *